(12) United States Patent
Ben-Asouli et al.

(10) Patent No.: US 7,279,278 B2
(45) Date of Patent: Oct. 9, 2007

(54) ORIENTATION-DIRECTED CONSTRUCTION OF PLASMIDS

(75) Inventors: Yitzhak Ben-Asouli, Kfar Hanagid (IL); Farhat Osman, Sachnin (IL)

(73) Assignee: Gene Bio-Application Ltd., Kfar Hanagid (IL)

( * ) Notice: Subject to any disclaimer, the term of this patent is extended or adjusted under 35 U.S.C. 154(b) by 368 days.

(21) Appl. No.: 10/636,509

(22) Filed: Aug. 6, 2003

(65) Prior Publication Data

US 2004/0209272 A1    Oct. 21, 2004

Related U.S. Application Data

(63) Continuation of application No. PCT/IL02/00104, filed on Feb. 11, 2002.

(30) Foreign Application Priority Data

Feb. 12, 2001    (IL) .................................... 141392

(51) Int. Cl.
*C12Q 1/68*    (2006.01)
*C12P 19/34*    (2006.01)

(52) U.S. Cl. ......................................... 435/6; 435/91.2

(58) Field of Classification Search .................... None
See application file for complete search history.

(56) References Cited

U.S. PATENT DOCUMENTS

| | | | |
|---|---|---|---|
| 4,459,359 A | | 7/1984 | Neurath |
| 4,683,195 A | | 7/1987 | Mullis et al. |
| 4,683,202 A | | 7/1987 | Mullis |
| 5,035,996 A | | 7/1991 | Hartley |
| 5,494,810 A | | 2/1996 | Barany et al. |
| 5,523,221 A | * | 6/1996 | Weiner ................. 435/91.2 |
| 5,824,516 A | * | 10/1998 | Collu et al. ............ 435/91.2 |
| 6,607,899 B2 | * | 8/2003 | Chui et al. ............. 435/91.2 |
| 6,641,998 B2 | * | 11/2003 | Sorge ..................... 435/6 |

FOREIGN PATENT DOCUMENTS

| EP | 812911 | 12/1997 |
|---|---|---|
| WO | WO98/10063 | 3/1998 |

OTHER PUBLICATIONS

Printout: pBluescript® example (http://www.stratagene.com/vectors/maps/pdf/pBluescript_SK_plus.pdf).*
Dooley et al. ("A rapid method to determine the orientation of blunt end ligated polymerase chain reaction products" Electrophoresis. Jul. 1993;14(7):662-3).*
Boyd ("Turbo cloning: a fast, efficient method for cloning PCR products and other blunt-ended DNA fragments into plasmids" Nucleic Acids Res. Feb. 25, 1993;21(4):817-21).*
Upcroft et al. ("Rapid and efficient method for cloning of blunt-ended DNA fragments" Gene. 1987;51(1):69-75).*
Coolidge et al. ("Run-around PCR: a novel way to create duplications using polymerase chain reaction" Biotechniques. May 1995;18(5):763-4).*
Beaucage And Carruther Tetraheoron Lett. 22:1859. Deoxynucleoside Phosphoramidites—A New Class Of Key Intermediates For Deoxypolynucleotide Synthesis, 1981, vol. 22, No. 20, No. 20. pp. 1859-1862.
Birnboim, H.C., et al., "A rapid alkaline extraction procedure for screening recombinant plasmids DNA", Nucleic Acids Research, 7:1513-1522 (1979).
Birnboim, H.C., A Rapid Alkaline Extraction Method for the Isolation of Plasmids DNA 100:243-255 (1983), Isolation Of Plasmid DNA.
Boyd, A.C.: "Turbo cloning: A fast, efficient . . . Plasmids", Nucleic Acids Research, vol. 21, No. 4, 1993, pp. 817-821; XP002184738, Oxford University Press.
Brown et al., (1979) Chemical Synthesis and Cloning of a Tyrosine tRNA Gene. pp.-109-151.
Bukhrashuili et al., "Comparison of initialing abilities of primers of different length in polymerization reactions catalyzed by DNA polymerases from thermoacidophilic archaebacteria", Biochem. Biophys. Acta, 1008:102-107 (1989).
Clark, J.M., Novel non-templated nucleotide addition reactions catalyzed by procaryotic and eucaryotic DNA polymerases, vol. 16, 1988, 20:9677, Nucleic Acids Research.
Dooley, Steven et al. "A rapid method to determine the orientation of blunt end ligated polymerase chain reaction products", vol. 14, No. 7 1993. pp. 662-63; XP-001041793, Electrophoresis.
Elie et al, "A DNA polymerase from a thermoacidophilic archaebacterium: evolutionary and technological interests", 951:261-267 (1988), Biochem, Biophys.

(Continued)

*Primary Examiner*—Kenneth R. Horlick
*Assistant Examiner*—Christopher M Babic
(74) *Attorney, Agent, or Firm*—Martin Fleit; Paul D. Bianco; Fleit Kain Gibbons Gutman Bongini & Bianco, P.L.

(57)    ABSTRACT

A method for orientation-directed construction of a construct including at least two nucleic acid segments of interest. Products are provided having phosphorylated blunt ends derived from the nucleic acid segments of interest. Separate ligation reactions are performed wherein in each reaction the phosphorylated blunt-ended products of two different segments obtained in the previous step are ligated to create a combined ligated sequence. PCR amplification reaction is performed using the combined ligated sequence obtained in the previous step as a template and specific enrichment primers direct the PCR amplification towards the desired orientation. Each combined ligated sequence is amplified in a separate reaction creating a combined product having phosphorylated blunt ends. The combined product is isolated and purified to have the enriched desired orientation. Self-ligation of the isolated purified combined product is performed to create a circular double-stranded DNA construct containing the desired segments properly aligned and operably linked.

22 Claims, 8 Drawing Sheets

OTHER PUBLICATIONS

Stefan et al, "Direct Cloning of PCR Products Amplified with Pwo DNA Polymerase", vol. 20 No. 2 1996. pp. 186-88, XP-002184735, BENCHMARKS.

Horton, et al., "Engineering hybrid genes without the use of restriction enzymes: gene splicing by overlap extension", 77:61-68 (1989), GENE.

Itakura et al., "Synthesis and Use of Synthetic oligonucleotides", 53:323-56, (1989) Ann. Rev. Biochem.

Kaluz, et al., "Directional cloning of PCR products using exonuclease III", Nucleic Acids Research, 20(16):4369-4370 (1992).

Kuijper, J.L., et al., "Functional cloning vectors for use in directional cDNA cloning using cohesive ends produced with T4 DNA polymerase", Gene 112: 147-155 (1992).

Loukianov, Evgeny et al: "Efficient cloning method . . . clones" Biotechniques, vol. 23, No. 2, 1997.

Mead et al., "A Universal method for the Direct Cloning of PCR Amplified Nucleic Acid", BioTechnology, vol. 9:657 (1991).

Narang et al., "Improved Phosphotriester Method for the Synthesis of Gene Fragments", Meth. Enzymol. (1979) 68:90.

Nisson, P.C., et al., "Rapid and Efficient Cloninig of PCR Products Using Uracil DNA Glycosylase", PCR Methods and Applications 1:120-123 (1991).

Shuldiner, et al., Ligase-Free Subcloning: A Versatile Method to Subclone Polymerase Chain Reaction (PCR) Products in a Single Day, Analytical Biochemistry 194:9-15 (1991).

Shuldiner A., et al., "PCR-induced (ligase-free) subcloning: a rapid reliable method to subclone polymerase chain reaction (PCR) products", Nucleic Acid Research, 18:1920 (1990).

Upcroft, P. et al: "Rapid and Efficient . . . Fragments" Gene (Amsterdam), vol. 51, No. 1, 1987.

Hitti, Youssef et al, "Proteinase K and T4 DNA Polymerase Facilitate the Blunt-End Subcloning of Products", vol. 16, No. 5, 1994, pp. 802-804-5, xp-02184736, Benchmarks.

* cited by examiner

Fig. 1

EcoRI dig.

95% bl.

95% gr.

```
                          SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: PRIMER 2037

<400> SEQUENCE: 1
gactctagag gatccccgg                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:PRIMER 2038

<400> SEQUENCE: 2
gacctgcagg catgcaagc                                                19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PRIMER 546

<400> SEQUENCE: 3
aatggctggt gatctttcag c                                             21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:PRIMER 547

<400> SEQUENCE: 4
tctaacatgt gtgtcgttc                                                19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:PRIMER 548

<400> SEQUENCE: 5
ttctgtgata aagggacc                                                 18
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:PRIMER 549

<400> SEQUENCE: 6
gcacttagtc tttgacc                                                        17

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:PRIMER 335

<400> SEQUENCE: 7
gaaccccgag tgacaagc                                                       18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:PRIMER 336

<400> SEQUENCE: 8
tcataccagg gcttggcc                                                       18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PRIMER 826

<400> SEQUENCE: 9
gcttcgtgct ttggactacc                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PRIMER 827

<400> SEQUENCE: 10
gggccccagg cagcagaacc                                                     20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:PRIMER 732

<400> SEQUENCE: 11
gctgtttcct gtgtgaa                                                        17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:PRIMER 110

```
<400> SEQUENCE: 12
agctgatacc gctcgccg                                                    18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:PRIMER 592

<400> SEQUENCE: 13
aatgagtaaa ggagaagaac                                                  20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:PRIMER 622

<400> SEQUENCE: 14
tatgaccatg attacgcca                                                   19
```

ORIENTATION-DIRECTED CONSTRUCTION OF PLASMIDS

RELATED APPLICATION

This application is a continuation of International Application No. PCT/IL02/00104 filed Feb. 11, 2002, the contents of which are here incorporated by reference in their entirety.

BACKGROUND OF THE INVENTION

1. Field of the Invention

The present invention relates to a method for orientation-directed construction of a construct comprising at least two nucleic acid segments of interest. More particularly, the present invention provides a rapid and versatile method for efficient cloning of constructs by PCR enrichment of the desired orientation.

2. Prior Art

Genetic vectors are one of the most important basic tools for research throughout the world in the fields of medicine, biology and biotechnology. Almost all studies in these fields require use of genetic vectors. Such genetic vectors are not only needed in research; for example, in medicine, genetic vectors are a means for undertaking gene therapy of diseases with a genetic background. This promising field is at the forefront of the latest medical developments, when the sequences of the human genome have been finally determined, availing a fantastic amount of information on new genes usable for genetic repair to every researcher in the world. In addition, biotechnologists use genetic vectors for the introduction of genes into various organisms in order to produce large quantities of the protein expressed by these genes. Agriculture also make use of genetic vectors, mainly in producing transgenic plants of improved yield or improved resistance to both pets and pesticides and for the extension of shelf life of agricultural products.

Genetic vectors are shuttles containing a DNA sequence encoding genetic information, expressed in-vivo in organisms such as bacteria, yeast, cell aggregates and transgenic animals, or in in-vitro systems. Genetic vectors are in most cases circular DNA segments known as plasmids, which contain genetic information, but there are also other genetic vectors such as viruses and transpoisons tailored for the purpose. The information borne by the vectors is tailored to their biological objective and to the biological environment into which the vector is introduced. A genetic vector may contain genetic segments from different sources. For example, a sequence of a gene encoding a mamalian protein may be inserted into bacterial sequences in order to form a genetic vector expressing the human protein in bacteria, so that by culturing the bacteria one would obtain large quantities of that human protein.

Vector construction encompasses a variety of recombinant DNA technology methods based on digesting and re-ligating DNA fragments. Insertion of new genes into target DNA fragments, is one of the most widely known uses for recombinant DNA technology. This procedure includes digestion of the target fragment (which comprises the vector sequence) with a restriction enzyme. Similarly, the insert DNA, carrying the gene of interest, is digested with the same enzyme or with an appropriate enzyme that leaves the same 3' or 5' overhanging. In one type of restriction enzyme digestion, cleavage of both the target DNA and insert DNA leaves overlapping 3' or 5' nucleotide fragments on each end. These overlapping fragments or "sticky ends" are well known properties of some restriction enzymes.

Further methods of directly cloning DNA fragments into target DNA sequences are available, as the method described by Mead et al. [Bio/Technology 9:657 (1991)]. This method is based on the ability of Taq polymerase to inherently add deoxyadenosine (dATP) to the 3' end of some newly synthesized duplex molecules described by Clark, J. M. [Nucleic Acids Research 20:9677 (1988)]. These single adenosine overhangs base pair with 3' thymidine (dTTP) overhangs at the insertion site of a specially designed vector. It has been found that even single base pairs are sufficient for hydrogen bonding two nucleotide sequences together.

In yet another method of inserting a nucleotide fragment into a target DNA, known as blunt-end ligation, fragments to be ligated are digested using restriction enzymes which do not leave any 3' or 5' overhanging nucleotides at the enzyme splice site. These enzymes are known as "blunt-end" enzymes due to this feature of their enzymatic activity. After digestion, blunt-end restriction enzymes maintain single 5' "terminal" phosphates on both sides of the restriction site. These terminal 5' phosphates are required by DNA ligase for any subsequent religation of the digested DNA sequence.

None of the aforementioned methods permits a researcher to choose and enhance a specific orientation for the segment of insert. This presents a distinct disadvantage in that the insert DNA can position itself at either of two 5' or 3' orientations with respect to the target nucleotide sequence.

In most procedures the insert orientation is critical, for example, ligation of a promoter sequence to heterologous gene for obtaining subsequent gene expression or producing chimeric genes or proteins, requires ligation in the correct orientation.

Moreover, most of the vectors will self-ligate, without the insert, in case no direction is provided for the insert. Furthermore, up to 50% of the genes on average, when inserted into different vectors, will ligate in the wrong orientation. This dramatically reduces the overall experimental efficiency. For this reason, many methods have been devised for preferentially cloning insert DNA fragments into target sequences in a preferred orientation. These methods are commonly known as directional cloning techniques.

Directional cloning is usually performed initially by digesting the target nucleotide sequences with two different restriction enzymes, resulting in molecules having dissimilar DNA ends at the target insertion site. The insert DNA is also digested using the same two restriction enzymes, thereby producing two dissimilar DNA ends that corresponded to a specific orientation in the target insertion site. By following this procedure, the insert DNA could only bind the target sequence in the desired orientation.

Although this method has been widely used in the art, it does have disadvantages. For instance, digesting both the target DNA and insert DNA with multiple restriction enzymes is very time consuming. In addition, multiple enzyme digestions increase the risk that either the target or insert DNA sequence will be cleaved at an internal restriction site in a specific manner, or unspecifically (star activity) or alternatively, would not be cleaved at all. Problems associated with digesting the ends of DNA strands, also charachterize digestion based methods, such as that required in cutting the insert sequence. Furtheremore, digestion using two different restriction endonucleases, requires changing buffers between each reaction, and decrease the probability of proper digestion of the DNA sequence. Moreover, the use of restriction enzymes in vector designing is a limiting factor in inserting sequences that may affect the flexibility of the desired construct.

Many investigators have attempted to improve methods relating to directionally cloning of DNA fragments, as detailed above. One of the most widely used procedures involving directional ligation relates to subcloning DNA fragments that have been amplified by the polymerase chain reaction (PCR).

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation. Thus, typical PCR cloning methods require preparation of PCR primer molecules attached to "add on" base sequences having a preferred restriction recognition sequence. Also, these methods can result in unintended internal restriction of uncharacterized or polymorphic sequences. Such limitations of previous methods add to the cost and complexity of cloning PCR products routinely.

Moreover, this protocol has the same drawbacks as the aforementioned double digestion method. In addition, the PCR primers have more bases to accommodate the restriction site that results in added expense for PCR primers. Additionally, this method is limited by the often inefficient cleavage of restriction endonuclease cleavage sites near an end of a double-stranded nucleic acid.

Another method of directionally cloning an insert into a target sequence uses Exonuclease III [Kaluz, et al., Nucleic Acids Research, 20(16):4369-4370 (1992)] to create the "sticky ends". In the method described by Kaluz et al., insert DNA fragments were digested with Exonuclease III. The number of nucleotides that Exonuclease III digests from the 3' end of DNA per minute is well known. After a timed digestion, the insert fragments were left with 5' overlapping nucleotide tails. These tails were engineered so that the 5' ends would only hybridize in one orientation upon base pairing to the target plasmid DNA molecule.

Nevertheless, the Exonuclease III method is specifically time-dependent and the enzyme continues to digest DNA as long as the reaction is incubated. For this reason, Exonuclease III might potentially digest through the end nucleotides and into the coding region of the insert DNA sequence, prompting an undesired experimental result.

In yet another method, production of sticky ends is performed using the 3' exonuclease activity of T4 DNA polymerase [Kuijper, J. L., et al. Gene 112: 147-155 (1992)], a further method of directionally cloning PCR generated fragments into a target DNA sequence based on incorporation of uracil into the PCR primers, followed by treatment with uracil-N-glycosylase [Nisson, P. C., et al. PCR Methods and Applications 1:120-123 (1991)].

Another example is disclosed in U.S. Pat. No. 5,523,221, directed at a method for directionally cloning an insert DNA sequence into a target DNA sequence. This method includes generating a monophosphorylated target DNA sequence and a monophosphorylated insert DNA sequence, followed by combining the insert DNA sequence, preferably with DNA ligase, with the target sequence. Thus, the insert sequence can only ligate in one orientation with respect to the target sequence. Preferably, the target DNA sequence is a plasmid. This method uses the calf intestinal alkaline phosphatese (CIAP) to produce monophosphate target DNA. The method has several disadvantage, the use of monophosphorylated target DNA and insert DNA significantly reduces the ligation efficiency and requires multiple restriction enzymes digestion.

All of the above directional cloning methods require multiple restriction enzyme digestion, addition of extra nucleotides to the insert, or are expensive and time consuming. For these reasons, there is a need for a simple, efficient, rappid and inexpensive method of directionally cloning a DNA fragment into its target sequence.

To solve the above mentioned complexity of endonucleases involvement, PCR technology has been used to engineer hybrid (chimeric) genes without the need to use restriction enzymes in order to segment the gene prior to hybrid formation. In this approach, fragments of the different genes that are intended to form the hybrid are generated in separate polymerase chain reactions. The primers used in these separate reactions are designed so that the ends of the different products of the separate reactions contain complementary sequences. When these separately produced PCR products are mixed, denatured and reannealed, the strands having matching sequences at their 3'-ends overlap, and act as primers for each other. Extension of this overlap by DNA polymerase produces a molecule in which the original sequences are spliced together to form the hybrid gene. Thus, this method requires specific primers each time one wishes to construct a chimeric molecule that contains the same fragments in different location or orientation. Furthermore, it does not allow a straightforward means to generate inverted or directly repeated DNA sequences [Horton, et al., Gene 77:61-68 (1989)].

Overall, current methods used for the construction of genetic vectors involve multi-step processes which are very time consuming. On average, the time required to introduce one genetic insert into an existing plasmid is more than three days. When a genetic vector is required to be assembled of several different genetic segments, its construction may take several weeks and more. In addition, when a genetic segment must be incorporated in a sequence in a definite orientation, the process complexity is increased and the products require a longer scanning time.

Ligase-free subcloning was reported as a rapid subcloning method [Shuldiner A., et al., Nucleic Acid Research, 18:1920 (1990) and Analytical Biochemistry 194:9-15 (1991)]. This procedure is performed by incorporating into the PCR primers sequences at the 5' ends that result in a PCR product whose 3' ends are complementary to the 3' ends of the recipient linearized plasmid. The PCR product and the plasmid are spliced together in a second PCR reaction in which Taq polymerase extends the complementary overlapping 3' ends. However, this method as well has several disadvantage compares to the method of the present invention. The primers designed for the ligase-free method should comprise sequences complementary to both segments of interest, and therefore these primers are quite long (about 50 nucleotides) expensive and having increased potential of non-specific annealing to the atmplate, whereas the primers designed for the present method should have the minimal length permitting specific annealing to the template. Furtheremore, the segments as well as the primers prepared for the present invention can be used for construction of different constructs. For example, a segment comprising an origin of replication and selectable marker, or even a certain reporter gene, can be ligated to different segments of interest in different constructs. These combined products can be enriched for the desired orientation by using the same primers, whereas the ligase-free method of Shuldiner et al., is limited in the specific direction and combination of segments. Thus, any different construct will require production of different products and synthesis of different primers, whereas the present invention is much more versatile and economic. Other disadvantages of the Shuldiner et al., ligase-free method are the necessity of extensive optimization of the number of PCR cycles of the second-stage PCR, the temperature at which heterologous reannealing and cyclization, the concentration of the NaCl. Most importantly, the reported efficiency of Shulinder et al., method is about 50% of the total number of the colonies, whereas the efficiency of the method of the present invention is about 95%. Furtheremore, successful subcloning with the Shulinder et al., method has been accomplished for PCR products as large as 1.7 kb. And finally, two of the primers used by the method of Shulinder et al., are complementary at their 3' end to the target sequence and at their 5' end to the plasmid. Thus, in order to insert the same fragment into two different plasmids about eight primers are required, whereas only six primers are needed for the OER method of the invention.

The present invention is based on the development of a rapid method designed to shorten and facilitate the process of constructing genetic vectors and streamlines this process, by providing genetic vectors aligned with their sequences in the proper orientation, without need for extensive scanning. The central process carried out in the method of the invention is designated as Orientation Enrichment Reaction (OER). In this process there is enrichment at every cycle, enreaches towards those vectors containing genetic segments aligned in the proper direction, so that at the end of the process a genetic vector, in which all segments are properly aligned, is obtained. Each cycle is made up of a phase of polymerase chain reaction, followed by product cleaning and then a stage of segment ligation. According to the method of the invention, an unlimited number of DNA segments may be ligated together whereby the size of the final segment obtained is the only restriction.

The method of the invention significantly shortens the time needed to construct a genetic vector, rendering construction of the vectors very easy and more versatile. On average, eight genetic segments may be ligated together overnight. When the directionality of the genetic vectors is examined, about 95% of them turn out to contain the required sequence with the proper orientation.

SUMMARY OF THE INVENTION

As a first aspect the present invention relates to a method for orientation-directed construction of a construct comprising at least two nucleic acid segments of interest, comprising the steps of:
  a. providing products having phosphorylated blunt ends, these products being derived from the nucleic acid segments of interest to be combined in the construct;
  b. performing separate ligation reactions, wherein in each reaction the phosphorylated blunt-ended products of two different segments obtained in step (a) are ligated, this ligation resulting in a combined ligated sequence, comprising two segments of interest attached together;
  c. performing PCR reaction using said combined ligated sequence obtained in step (b) as a template and specific enrichment primers directing said PCR amplification towards the desired orientation, each combined ligated sequence being PCR amplified in a separate reaction to create a combined product having phosphorylated blunt ends;
  d. isolating and purifying the combined product obtained in step (c), this combined product having the enriched desired orientation;
  e. optionally, cyclically repeating steps (b) to (d) for a desired number of times, to combine all the segments of interest, such cyclic repetition of ligation of products being followed by orientation enrichment PCR, and enabling the combination of all the segments of interest in order create the final isolated combined product having all segments aligned in the desired orientation; and
  f. performing self-ligation of the final isolated purified combined product obtained in step (d) or (e), creating a circular double-stranded DNA construct containing all the desired segments properly aligned and operably linked to each other.

In a specific embodiment, the method of the invention is intended for orientation-directed construction of a construct comprising at least two segments. One of the segment of interest comprises a replicable segment and in some embodiments this segment may also contain sequences coding for a selectable marker. Alternatively, any other segment of interest may comprise the sequences coding for a selectable marker.

The replicable segment contained in one of the segments of interest comprises an origin of replication (ori) sequence.

According to a specific embodiment of the present invention the replicable segment may be derived from a replicable vector selected from the group consisting retroviral vectors, phage vectors, plasmid vectors, expression vectors, self replicating vectors, transposition elements, phagemid vectors and YAC vectors.

According to a specificly preferred embodiment, the phosphorylated blunt-ended products of step (a) of the method of the invention may be obtained by different procedures, for example:
  (i) performing a first set of PCR amplification using said segments as template, to create products having phosphorylated blunt ends, each segment being amplified in a separate reaction, using specific primers; or
  (ii) creating blunt end products by cleavage of the nucleic acid segments of interest by a blunt-end endonuclease; or
  (iii) creating cohesive end products by cleavage of said nucleic acid segments employing a sticky-end endonuclease, followed by fill-in reaction; or
  (iv) creating cohesive end products by cleavage of said nucleic acid segments employing a sticky-end endonuclease, followed by single-strand DNA endonuclease reaction, degrading single-strand extensions from the DNA ends.

In case the blunt ended products are obtained by PCR reaction, a phosphorylation reaction should be performed. Phosphorylation reaction employing T4 polynucleotide kinase may be performed on the blunt end PCR products or preferably, on the primers used for the PCR reaction.

In yet another embodiment, the present invention relates to a method for orientation-directed construction of a construct comprising more than two nucleic acid segments. Similarly to the steps involved in combining of two segments, combining of more than two segments involves cyclic repetition of steps (a) to (d) of the method of the invention, to create isolated combined products having the desired orientation. These combined products are then ligated to create a combined ligated sequence. In each ligation reaction only two of the combined products, obtained in the cyclic repetition of the steps of the method, are ligated. The next step involves PCR reaction using said ligated sequence as a template and specific enrichment primers directing this PCR amplification towards the desired orientation. The combined products obtained, having the desired orientation, are then isolated and purified.

The steps mentioned herein above may be repeated cyclically for a desired number of times to create a combined product containing all the segments of interest aligned in the desired orientation to create a final combined product. The final step is self-ligation of the isolated final combined product, for creation of a circular double-stranded DNA construct containing all the desired segments properly aligned and operably linked to each other.

According to another preferred embodiment, the method of the invention employs as specific primers for the first set of PCR amplification reactions, a 5' primer comprising a sequence derived from the 5' end of the segment of interest (sense primer) and a 3' primer which is complementary to the sequence of the 3' end of the specific segment to be amplified (anti-sense primers).

Further, the specific enrichment primers employed in the amplification of the combined ligated sequences according to the method of the invention, may be: a 5' primer comprising sequence derived from 5' end of the first segment, which is upstream to the second ligated segment in the combined ligated product (sense primer) and a 3' primer which is complementary to the 3' end sequence of the second ligated segment (anti-sense primer), of the combined ligated sequence.

Another preferred embodiment relates to the primers used in the method of the invention. Each of said primers may comprise from about 4 to about 200 nucleotides in length. More preferably, each of said primers comprises from 5 to about 50, and most preferably, said primers comprise from about 8 to about 30 nucleotides in length.

Specifically preferred embodiments of the present invention relate to the enzymes employed by the method of the invention. For example, ligation reaction may be performed by employing DNA ligase and PCR amplification may be performed by employing a high fidelity DNA polymerase.

According to a specific embodiment, the method of the invention is intended for constructing a construct comprising at least two segments of interest. Such segments may be the following: one of said segments of interest comprises an origin of replication (ori) sequence and optionally a sequence coding for a selectable marker; at least one additional segment comprising a heterologous or homologous coding nucleic acid, or mutations, fragments or derivatives thereof and optionally a selectable marker; and optionally, at least one additional segment comprising nucleic acid sequences coding for expression, control, promoting and/or regulatory elements.

The heterologous or homologous coding sequence of interest may encode a protein selected from the group consisting of reporter proteins, enzymes, hormones, growth factors, cytokines, structural proteins and industrially applicable proteins, or is itself a therapeutic product. According to another specific embodiment, the heterologous coding sequence may encode a reporter protein selected from the group consisting of green fluorescent protein (GFP), luciferase, secreted alkaline phosphatase (SEAP) and β-galactosidase (β-gal).

Constructs containing a heterologous or homologous coding sequence may be, according to a specific embodiment of the invention, expression vehicles.

According to a preferred embodiment, the method of the invention may be performed manually.

According to another preferred embodiment, the method of the invention may be performed automatically.

BRIEF DESCRIPTION OF THE FIGURES

FIG. 1 Schematic illustration of the OER method

Ligation of two PCR products (fragments I and II), performed using a ligase, produced four different possible orientations (A, B, C, D). Enrichment for the desired orientation was performed by PCR reaction using specific primers. The 5' primer is a sense primer derived from the 5' end of the upstream segment and the 3' primer is an antisense primer derived from the 3' end of the downstream segment. Abbreviations: OER (orientation enrichment reaction), frag. (fragment), Lig. (ligation).

Figure 2A:
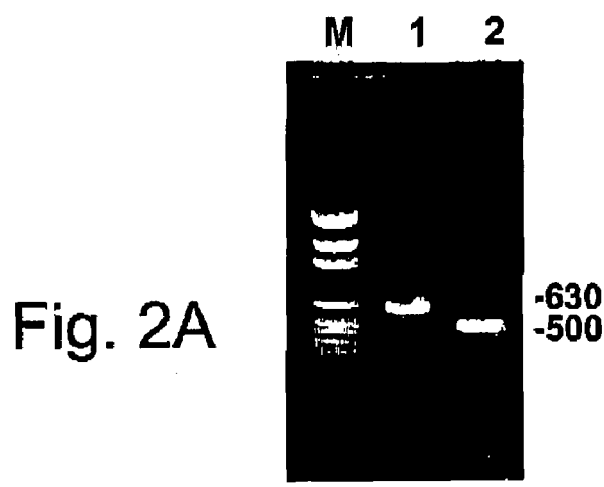
Figure 2B:
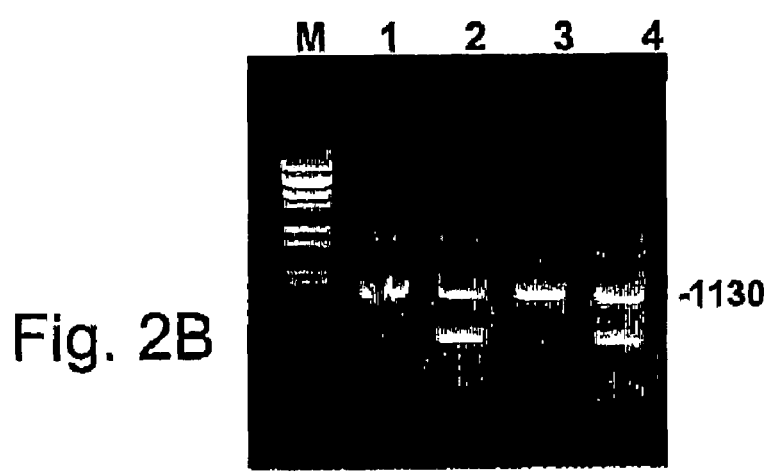
Figure 2C:
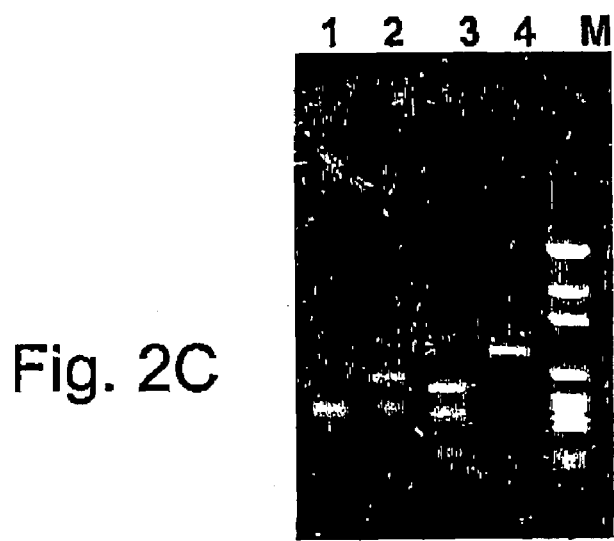

FIGS. 2A-2C construction of construct having the four possible orientations using the OER method FIG. 2A PCR of two DNA segments, 1: PCR of the first segment using primers 335 and 336 (SEQ ID NOs:7 and 8, respectively) to generate a DNA segment of 630 nucleotide size; 2: PCR of the second segment using primers 826 and 827 (SEQ ID NOs:9 and 10, respectively) to generate segment of 500 nucleotide size; M: DNA marker of λ/BstE II.

FIG. 2B PCR for the ligation products of two DNA segments having undergone PCR at A, 1-4: PCR for the splicing products of the two segments with the four possible orientations (335-826, 335-827, 336-826, 336-827, respectively); a segment of 1130 size is obtained by linking the two previous segments; M: DNA marker of λ/BstE II.

FIG. 2C Analysis of the orientation of inserted segments using restriction enzymes. Cleavage of PCR products using the restriction enzyme PvuII; the Figure shows that a different cleavage pattern is obtained for the four different orientations; M: DNA marker.

Figure 3A:
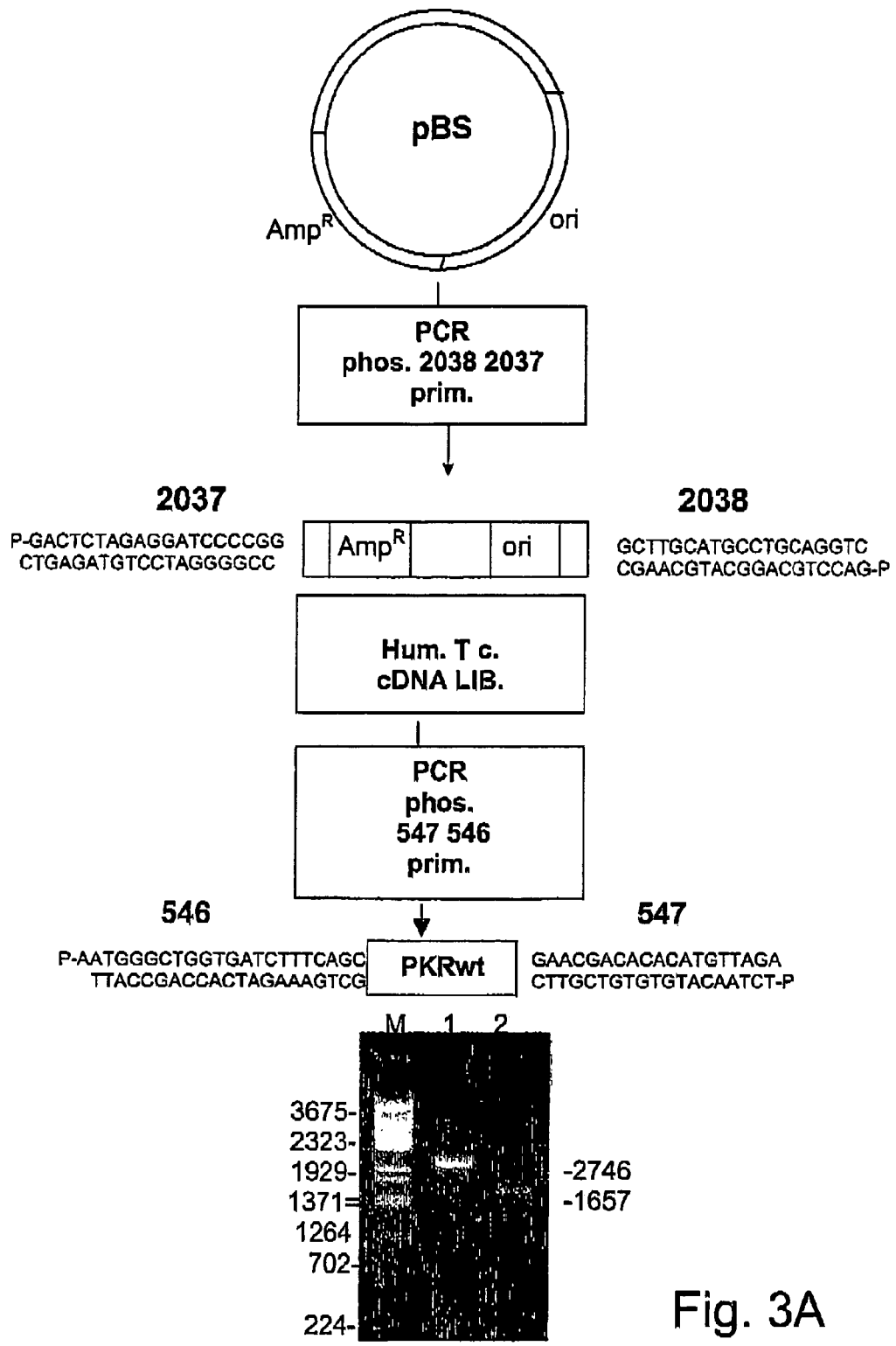
Figure 3B:
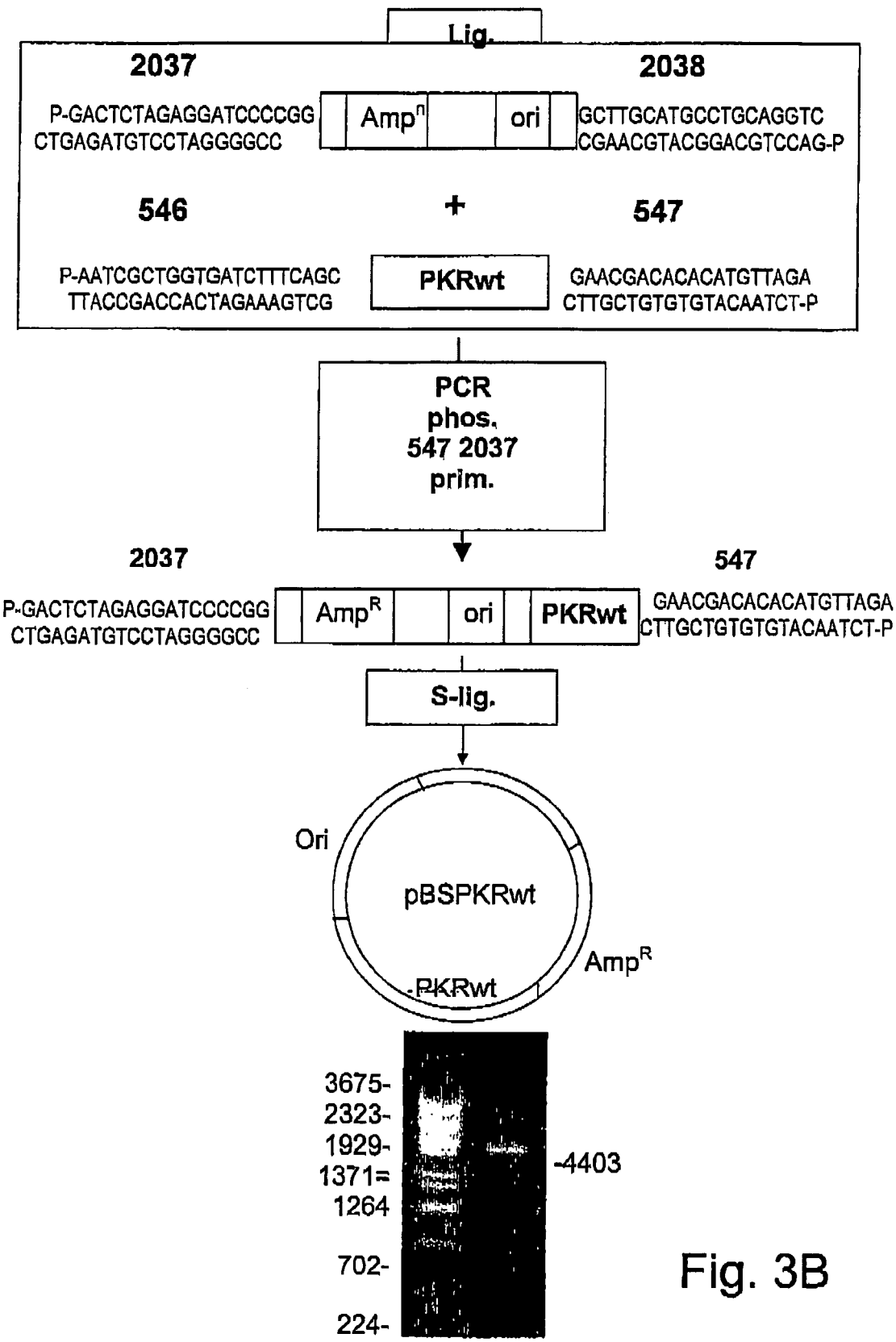
Figure 3C:
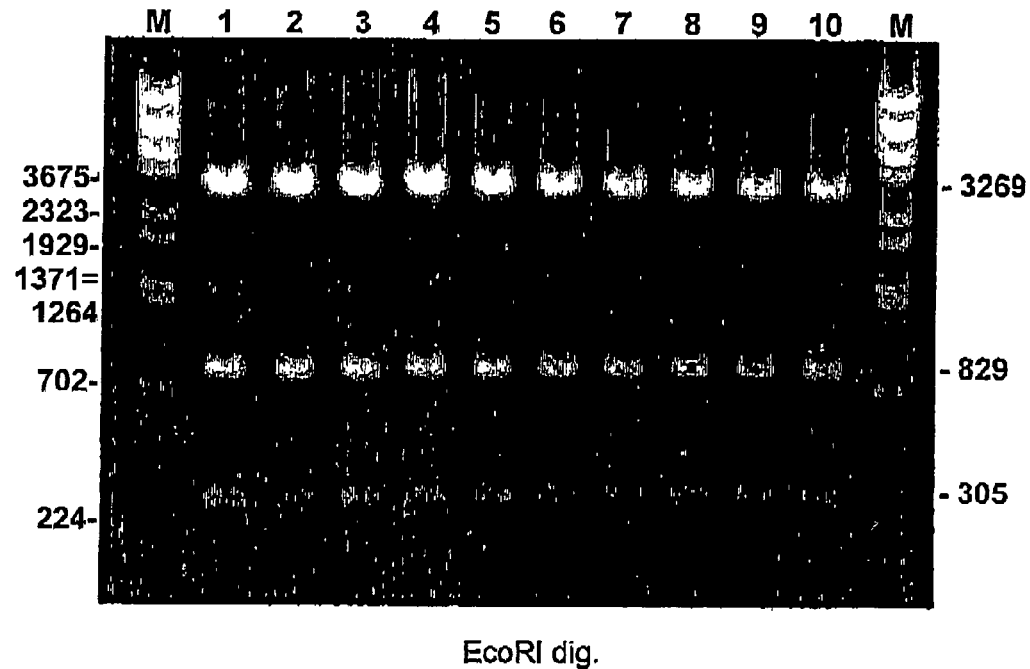
Figure 3C:
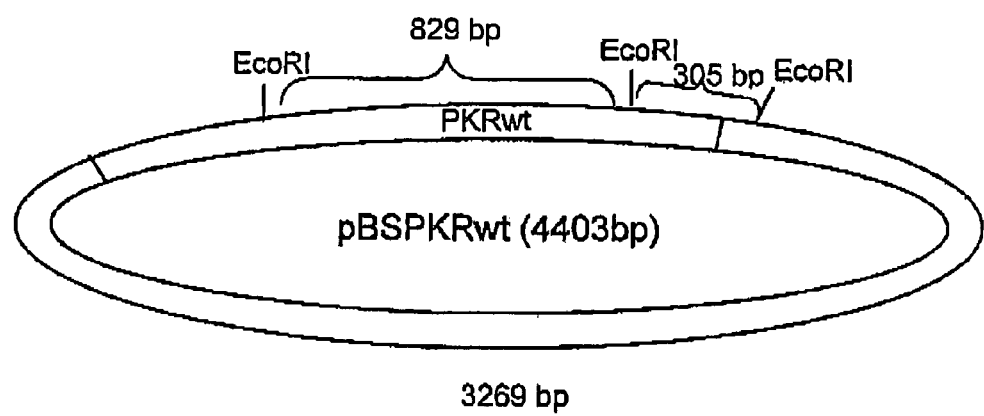

FIGS. 3A-3C construction of the pcDNAPKRwt construct using the OER method

FIG. 3A Top: schematic illustration showing the preparation of the first segment using primers 2037 and 2038 (SEQ ID NO:1 and 2, respectively) and the preparation of the second segment using primers 546 and 547 (SEQ ID NO:3 and 4, respectively). Bottom: Agarose gel showing the PCR products of the first amplification reaction creating the first and second segments (2746 bp and 1657 bp, respectively).

FIG. 3B Top: schematic illustration showing creation of the third segment by ligating segments 1 and 2 and enriching for the desired orientation by performing PCR using the 2037 and 547 primers (SEQ ID NO:1 and 4, respectively). Bottom: Agarose gel showing the PCR product of the third segment (4403 bp), which is the combined product of the first and the second products.

FIG. 3C Top: PKR wt mini-preparation analysis of the colonies. Bottom: illustration showing a schematic map of the resultant final plasmid.

Abbreviations: phos. (phosphorylated), Hum. (human), c. (cell), lib. (library), prim. (primers), Amp (ampicillin), ori (origin of replication), S-lig. (self ligation), dig. (digestion).

Figure 4A:
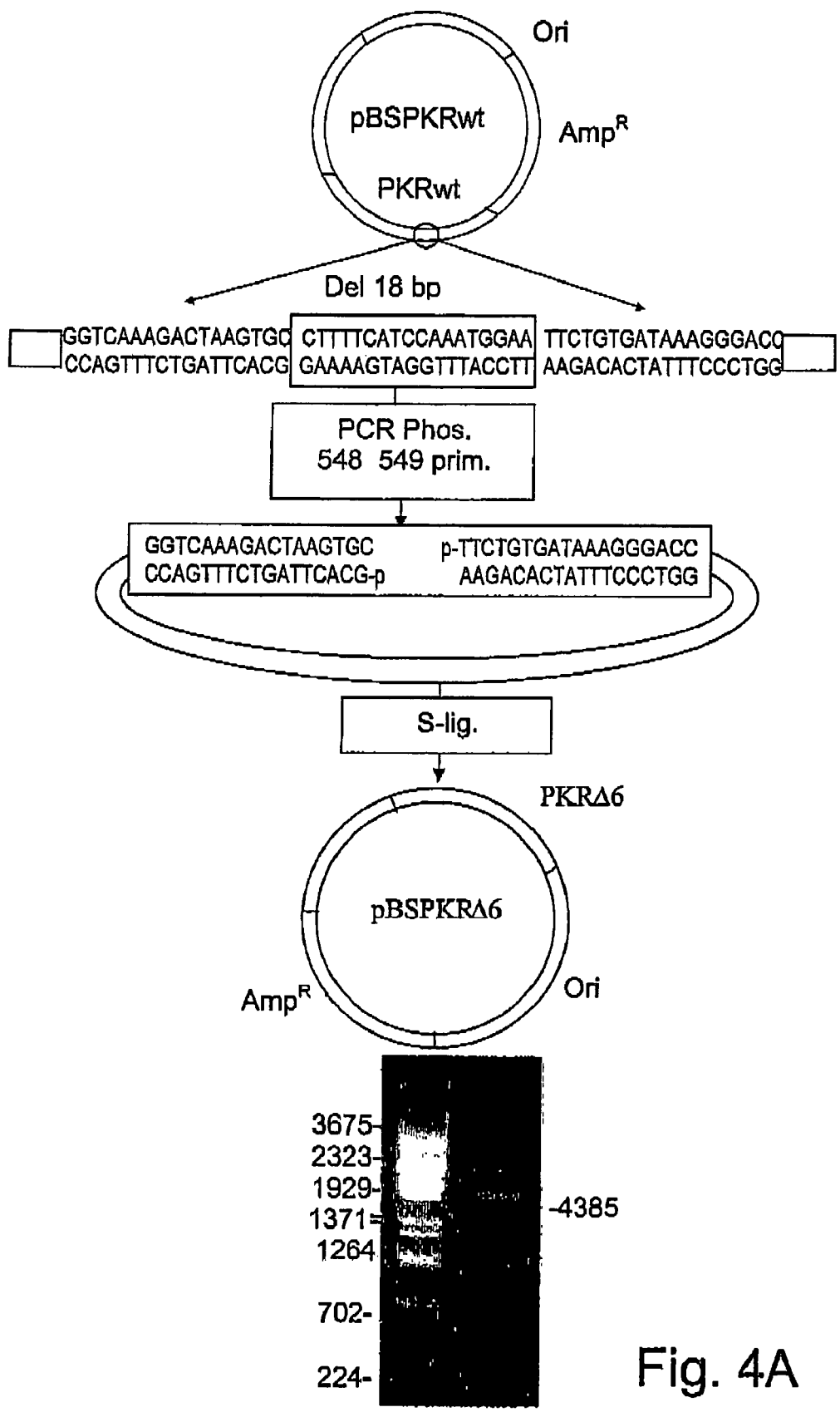
Figure 4B:
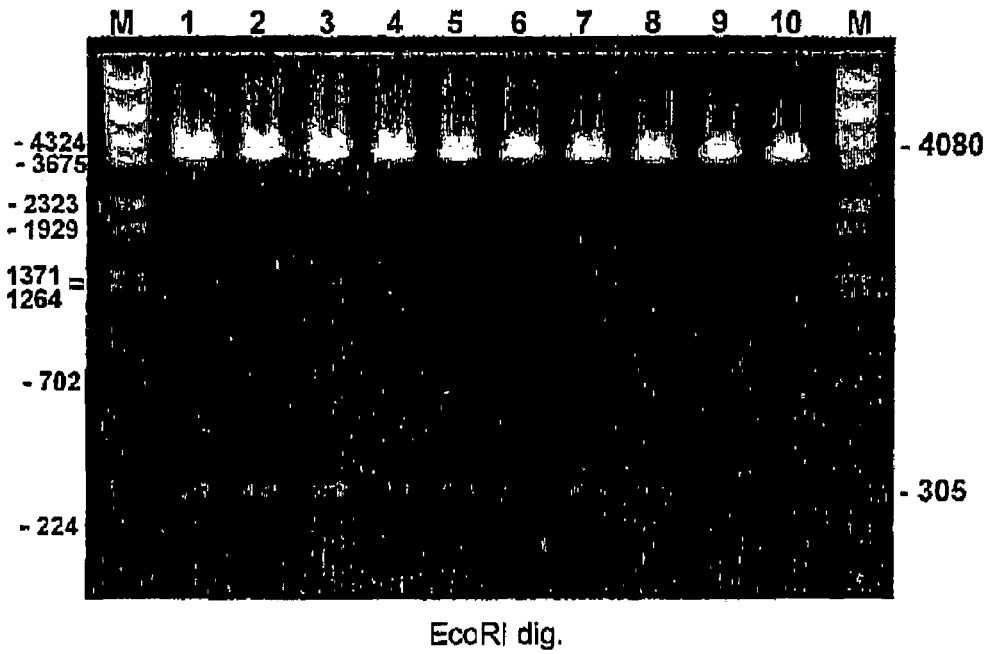
Figure 4B:
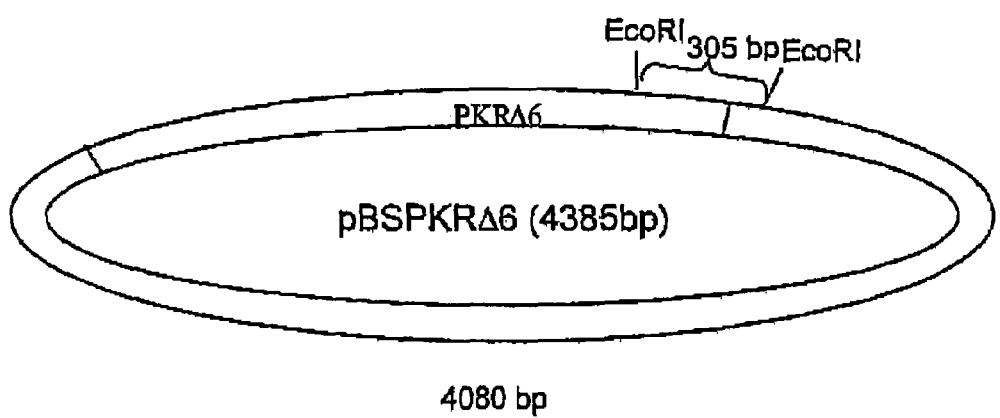

FIGS. 4A-4B Construction of the pcDNA-PKRΔ6 construct using the OER method

FIG. 4A Top: schematic illustration showing creation of a segment containing the deletion mutation. The segment was prepared by performing PCR using primers 548 and 549 (SEQ ID NOs: 5 and 6, respectively) and the plasmid pcDNAPKRwt (that was created above) as a template. The product of PKR□6 is shown. Bottom: Agarose gel showing the PCR product of the final segment (4385 bp) containing deletion of 18 nucleic acids.

FIG. 4B Top: Agarose gel showing digestion products of the PKR□6 plasmid obtained after mini-preparation. Bottom: illustration showing a schematic map of the resultant final plasmid. Abbreviations: phos. (phosphorylated), prim. (primers), Amp (ampicillin), ori (origin of replication), S-lig. (self ligation), dig. (digestion), del. (deletion), bp (base pairs).

Figure 5A:
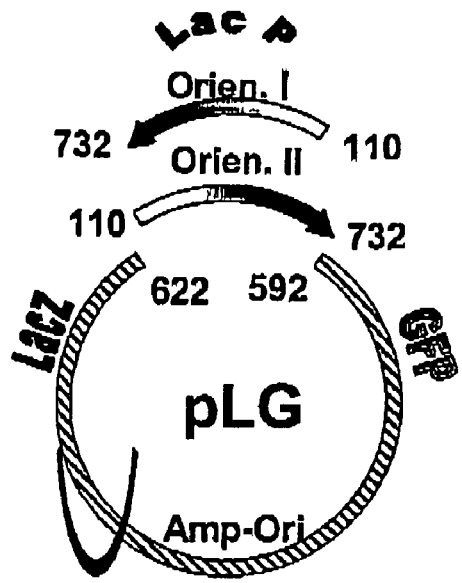

FIGS. 5A-5E Schematic illustration of using the OER method in constructing two different constructs from the same template FIG. 5A The pGFP-LacP-LacZ and the pLacZ-LacP-GFP plasmids, both carrying the IPTG induced promoter (LacP) were constructed using a single template in two different orientations, by the OER method of the invention.

Figure 5B:
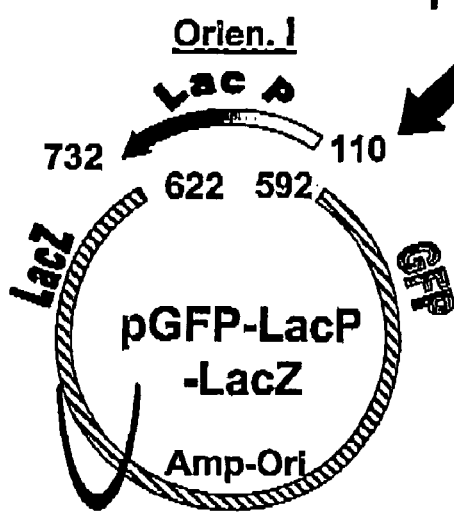

FIG. 5B Insertion of the LacP promoter and enrichment of orientation I, results in LacZ expression.

Figure 5C:
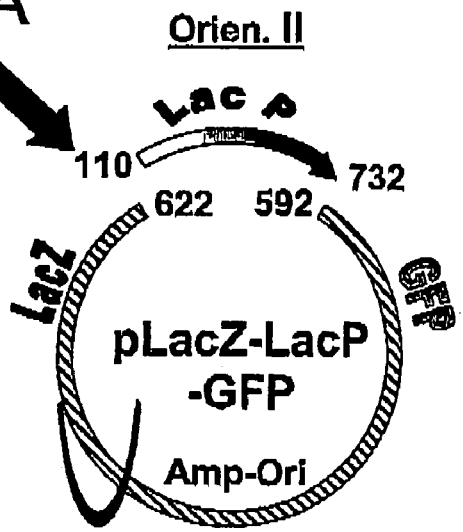

FIG. 5C insertion of the LacP promoter and enrichment of orientation II, results in GFP expression.

Figure 5D:
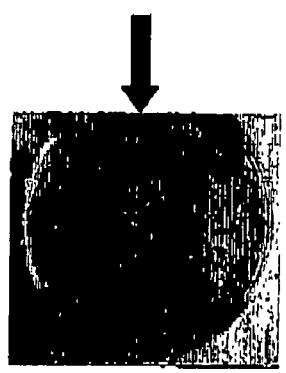

FIG. 5D about 95% of the bacteria transformed with the pGFP-LacP-LacZ construct, produced by enriching for orientation I, resulted in colonies displaying a blue color.

Figure 5E:
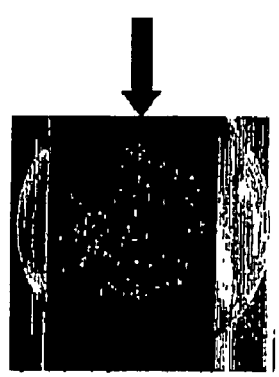

FIG. 5E about 95% of the bacteria transformed with the pLacZ-LacP-GFP construct, produced by enriching for orientation II, resulted in colonies displaying a green fluorescent signal under U.V light.

Abbreviations: Orien. (orientation), LacP (IPTG induced promoter), GFP (green fluorescent protein), LacZ (β-galactosidase gene), Amp (ampicillin) Ori (origin of replication), bl. (blue), gr. (green)

DETAILED DESCRIPTION OF PREFERRED EMBODIMENTS OF THE INVENTION

Most of the cloning techniques of nucleic acid sequences involve the use of PCR. These methods allows for easy cloning of any nucleic acid sequence flanked by known sequences, by designing primers which contain restriction endonuclease cleavage sequences. After amplification, the double-stranded PCR product can be digested with the corresponding endonuclease to obtain small 5' or 3' overhang sequences characteristic of the endonucleases. The PCR products are ready for cloning into a vector digested with the same endonuclease. However, these methods are limited by the often inefficient cleavage of restriction endonuclease cleavage sites near an end of a double-stranded nucleic acid. Further, it is well known to those of skill in the art that recombinant clones with linker DNA (containing a variety of restriction sites) have reduced E. coli transfection efficiencies. The cloning method of the present invention is advantageous, since it does not involve use of restriction enzymes and therefore, does not require insertion of DNA linkers. For this reason, transfection efficiencies of clones produced by the method of the present invention are greater than those produced by other techniques requiring the use of DNA linkers.

Thus, as a first aspect the present invention relates to a method for orientation-directed construction of a construct comprising at least two nucleic acid segments of interest. In a first step, products having phosphorylated blunt ends are provided. These products are derived from the nucleic acid segments of interest that is intended to be combined in the final construct. Phosphorylated blunt-ended segments may be obtained by using variety of procedures as will be described herein below. In a next step, separate ligation reactions are performed to combine two segments of interest. In each reaction, the phosphorylated blunt ended products of two different segments obtained in the first step are ligated. This ligation creates a combined ligated sequence, comprising two segments of interest attached together. As shown in the illustrative example in FIG. 1 and in the experiment presented in FIG. 2 (see Example 1), ligation of two double-stranded segments may result in products having four possible different orientations. The next step therefore, would be enrichment of the desired orientation in the resultant product population, which may be achieved by performing a PCR reaction using the ligated sequence obtained in the second step of the method of the invention method as a template and specific enrichment primers directing the PCR amplification towards the desired orientation. Each combined ligated sequence is PCR amplified in a separate reaction, to create combined product having the desired orientation as well as phosphorylated blunt ends. In a fourth step, the combined product obtained in the third step is isolated and purified. This combined product has the enriched desired orientation. If the desired construct is composed of more than two segments, the second to fourth steps may be cyclically repeated for any desired number of times, to combine all the segments of interest. The number of times of repeating these steps depends upon the number of segments to be ligated. The cyclic repetition of ligation of products followed by orientation enrichment PCR, will enable the combining of all segments of interest in order to create the final isolated combined product having all segments aligned in the desired orientation. The final step is performing self-ligation of the linear final isolated purified combined product obtained in the former step, creating a circular double-stranded DNA construct containing all the desired segments properly aligned and operably linked to each other. It is to be appreciated that in case that a linear product is desired, there is no need for said self-ligation step.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA—dependent DNA polymerase).

The term "operably linked" is used herein for indicating that a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein "PCR" (polymerase chain reaction) refers to a process of amplifying one or more specific nucleic acid sequences by repeated rounds of synthesis and denaturing under appropriate "amplification conditions".

PCR requires two primers that are capable of hybridizing with a single-strand of a double-stranded target nucleic acid sequence which is to be amplified under appropriate "hybridization conditions". In PCR, this double-stranded target sequence is denatured and one primer is annealed to each single-strand of the denatured target. The primers anneal to the target nucleic acid at sites removed (downstream or upstream) from one another and in orientations such that the extension product of one primer, when separated from its complement, can hybridize to the extension product generated from the other primer and target strand.

Once a given primer hybridizes to the target sequence, the primer is extended by the action of a DNA polymerase. DNA polyermase which is heat stable is generally utilized so that new polymerase need not be added after each denaturation step. Such thermostable DNA polyermase would be known to one of ordinary skill in the art, for example is may be Taq polymerase. The extension product is then denatured from the target sequence, and the process is repeated. One particular method for minimizing the effects of cross-contamination of nucleic acid amplification is described in U.S. Pat. No. 5,035,996, incorporated herein by reference. U.S. Pat. No. 5,494,810 to Barany et al., entitled "Polymerase chain reaction (PCR)", incorporated herein by reference, refers to a patented process (described in U.S. Pat. Nos. 4,683,202 and 4,683,195) for the exponential amplification of a specific DNA fragment by utilizing two oligonucleotide primers that hybridize to opposite strands and flank the region of interest in a target DNA. U.S. Pat. No. 4,459,359, also incorporated by reference, and describes PCR assays.

As used herein "amplification conditions" are those conditions under which a nucleic acid molecule may hybridize with two oligonucleotide primers which have some homology to the nucleic acid molecule, and through primer extension, replicate the nucleic acid molecule making a single-stranded nucleic acid molecule into a double stranded nucleic acid molecule via primer extension. This is elongation. The two strands are then melted apart by raising of the temperature and the single strands are again available for hybridization with a homologous single stranded oligonucleotide primer. Such conditions are well known to one of ordinary skill in the art and are described in more detail for certain specific nucleic acid molecules hereinbelow.

As used herein, "hybridization conditions" include temperatures, salt concentrations, primer sequences, nucleic acid sequences, solvent concentrations that allow two single-stranded nucleic acid molecules to base pair via hydrogen bonding as described by Watson and Crick. These conditions will be specific for each set of nucleic acids and primers. However, general conditions are well known to one of skill in the art and are described and referenced more fully below.

The PCR mixture may contain the target DNA, the DNA primer pairs, four deoxyribonucleoside triphosphates (A, T, C, G), $MgCl_2$, DNA polymerase (thermostable), and conventional buffers. The DNA can be amplified for a number of cycles (usually from 20-40 cycles). It is generally possible to increase the sensitivity of detection by using a multiplicity of cycles, each cycle consisting of a short period of denaturation of the target DNA at an elevated temperature, cooling of the reaction mixture, and polymerization with the DNA polymerase. Choosing PCR primer sequences, preparing PCR reagents and reaction mixtures, and designing and running PCR are well known procedures in the PCR art.

Briefly, enzyme, primers, target nucleic acid, dNTPs, $MgCl_2$ and buffer are mixed into a reaction mixture. the tube is placed in a thermal cycler, many versions of which are commercially available from suppliers such as Perkin Elmer Cetus Instruments, and heated to a temperature between about 50° C. and about 80° C., preferably between 70° C. and 80° C.

As used herein, "amplification" is a special case of nucleic acid replication involving template specificity. Template specificity is here distinguished from fidelity of replication (i.e., synthesis of the proper polynucleotide sequence) and nucleotide (ribo- or deoxyribo-) specificity.

Detection of amplified nucleic acid product can be accomplished by any of a variety of well known techniques. In a preferred embodiment described in step (d) in the method of the invention, the amplified product is separated on the basis of molecular weight by gel electrophoresis, and the separated products are then visualized by the use of nucleic acid specific stains which allow one to observe the discrete species of resolved amplified product present in the gel. Although numerous nucleic acid specific stains exist and would be suitable to visualize the electrophoretically separated nucleic acids, ethidium bromide is preferred.

In a specific embodiment, the method of the invention is intended for orientation directed constructing of a construct comprising at least two segments. One of the segments of interest comprises a replicable segment and in some embodiments this fragment may also contain sequences coding for a selectable marker. Alternatively, any other segment of interest may comprise the sequences coding for a selectable marker. The replicable segment contained in one of the segments of interest comprises an origin of replication (ori) sequence.

As used herein replicable segment or prokaryotic replicon means a DNA sequence having the ability to direct autonomous replication and maintenance of the recombinant DNA molecule extrachromosomally in a prokaryotic host cell, such as a bacterial host cell, transformed therewith. Such replicons are well known in the art. According to a specific embodiment of the present invention, the replicable segment may be derived from a replicable vector selected from the group consisting retroviral vectors, phage vectors, plasmid vectors, expression vectors, self-replicating vectors, transposition elements, phagemid vector YAC vectors.

In addition, those embodiments that include a procaryotic replicon may also include a selectable marker, which is for example a gene whose expression confers drug resistance to a bacterial host transformed therewith. Typical bacterial drug resistance genes are those that confer resistance to ampicillin, tetracycline, or kanamycin.

A variety of selectable markers can be incorporated into any construct. For example, a selectable marker which confers a selectable phenotype such as drug resistance, nutritional auxotrophy, resistance to a cytotoxic agent or expression of a surface protein, can be used. Selectable marker genes that can be used include neo, gpt, dhfr, ada, pac, hyg, CAD, and hisD. The selectable phenotype conferred makes it possible to identify and isolate recipient cells. Amplifiable genes encoding selectable markers (e.g., ada, dhfr and the multifunctional CAD gene which encodes carbamyl phosphate synthase, aspartate transcarbamylase, and dihydro-orotase) have the added characteristic that they enable the selection of cells containing amplified copies of the selectable marker inserted into the genome. This feature provides a mechanism for significantly increasing the copy number of an adjacent or linked gene for which amplification is desirable.

Selectable markers can be divided into two categories: positively selectable and negatively selectable (in other words, markers for either positive selection or negative selection). In positive selection, cells expressing the positively selectable marker are capable of surviving treatment with a selective agent (such as neo, gpt, dhfr, ada, pac, hyg, mdrl and hisD). In negative selection, cells expressing the negatively selectable marker are destroyed in the presence of the selective agent (e.g. tk, gpt).

It is to be apreciated that the method of the invention may be used for creation of a fragment comprising different number of segments of interest, properly alinghed in a desired orientation. This fragment may be then inserted to an existing linearized vector, to create the construct of interest by using conventional cloning techniques.

Examples for conventional cloning techniques include use of restriction endonucleases followed by ligation, as described in Maniatis et al, Molecular Cloning: A Laboratory Manual, Cold Spring Harbor Laboratory, incorporated herein by reference.

According to a specificly preferred embodiment, the phosphorylated blunt ended products of the first step of the method of the invention may be obtained by different procedures, for example:
(i) performing a first set of PCR amplification using said segments as template to create products having phosphorylated blunt ends, each segment amplified in a separate reaction, using specific primers; or
(ii) creating blunt end products by cleaving the nucleic acid segments of interest by a blunt-end endonuclease such as Srfl (GCCC/GGGC), Smal (CCC/GGG) or EcoRV (GAT/ATC); or
(iii) creating cohesive end products by cleaving osaid nucleic acid segments employing a sticky-end endonuclease, followed by fill-in reaction; or
(iv) creating cohesive end products by cleavage of said nucleic acid segments employing a sticky-end endonuclease, followed by single-strand DNA endonuclease reaction, degrading single-strand extensions from the DNA ends.

After digestion, blunt-end restriction enzymes maintain single 5' "terminal" phosphates on both sides of the restriction site.

In case the blunt ended products are obtained by PCR reaction, phosphorylation reaction should be performed. It should also be appreciated that there are many alternative methods for producing a phosphorylated DNA segment. For example, the enzyme polynucleotide kinase is used by those with skill in the art to add phosphate groups to the 5'-end of DNA molecules. Phosphorylation reaction employing T4 kinase may be performed on the blunt end PCR products or preferably, on the primers used for the PCR reaction.

In yet another embodiment, the present invention relates to a method for orientation-directed construction of a construct comprising more than two nucleic acid segments. Similarly to the steps involved in combining of two segments, combining more than two segments involves cyclic repetition of steps (b) to (d) according to the method of the invention, to create isolated combined products having the desired orientation. These combined products are then ligated to create a combined ligated sequence. In each ligation reaction only two of the combined products obtained in the cyclic repetition are ligated. The next step involves a PCR reaction using said ligated sequence as a template and specific enrichment primers directing this PCR amplification towards the desired orientation. The combined products obtained, having the desired orientation, are then isolated and purified.

The steps may be repeated cyclically for a desired number of times to create a final combined product containing all the segments of interest aligned in the desired orientation. The final step is self-ligation of the isolated final combined product, for creation of a circular, double-stranded DNA construct containing all the desired segments properly aligned and operably linked to each other.

The method of the invention preferably employs as specific primers for the first set of PCR amplification reactions, a 5' primer comprising a sequence derived from the 5' end of the segment of interest (sense primer) and a 3' primer which is complementary to the sequence of the 3' end of the specific segment to be amplified (antisense primers).

Further, the specific enrichment primers employed in the amplification of the combined ligated sequences according to the method of the invention, may be: a 5' primer comprising sequence derived from 5' end of the first segment, which is upstream to the second ligated segment in the combined ligated product (sense primer) and a 3' primer which is complementary to the 3' end sequence of the second ligated segment (antisense primer) of the combined ligated sequence.

The term complementary nucleotide sequence as used herein relates to a sequence of nucleotides in a single-stranded molecule of DNA or RNA that is sufficiently complementary to another single strand to specifically (non-randomly) hybridize to it with consequent hydrogen bonding.

By hybridization is meant the pairing of complementary nucleotide sequences (strands of nucleic acid) to form a duplex, heteroduplex, or complex containing more than two single-stranded nucleic acids, by establishing hydrogen bonds between complementary base pairs. Hybridization is a specific, i.e. non-random, interaction between/among complementary polynucleotides that can be competitively inhibited.

Figure 1:
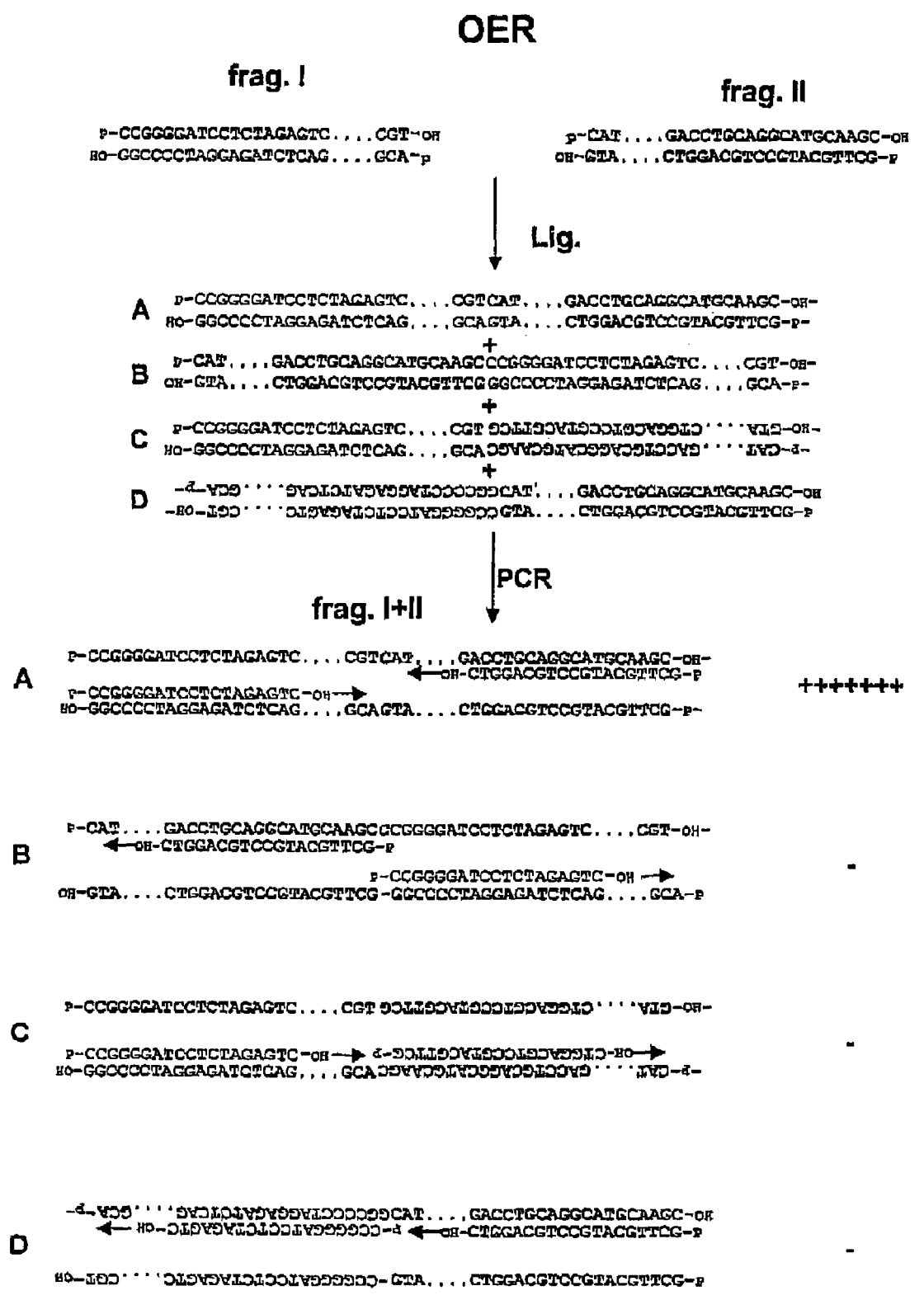

It should be noted that the same primers can be used for the first PCR reaction creating the blunt ended segment of interest, and the orientation enriching PCR reaction, as exemplified in FIG. 1, and in Examples 1 and 2.

The term primer as used herein is: a polynucleotide, whether purified from a nucleic acid restriction digest or produced synthetically, that is capable of acting as a point of initiation of synthesis when placed under conditions in which synthesis of a primer extension product complementary to a template nucleic acid strand is induced, i.e., in the presence of nucleotides and an agent for polymerization, such as DNA polymerase, reverse transcriptase and the like, under suitable temperature and pH reaction conditions.

Oligonucleotides or polynucleotides for use as PCR primers may be chemically synthesized according to the solid phase phosphoramidite triester method first described by Beaucage and Carruthers [Tetrahedron Lett. 22:1859-1862 (1981)] using an automated synthesizer, as described in Needham-VanDevanter [Needham-VanDevanter, D. R., et al., Nucelic Acids Res. 12:6159-6168 (1984)]. Purification of oligonucleotides is by either native acrylamide gel electrophoresis or by anion-exchange HPLC. The sequence of the synthetic oligonucleotide can be verified using the chemical degradation method of Maxam and Gilbert [Maxam, A. M. and Gilbert, W. Methods in Enzymology Grossman, L. and Moldave, D., eds., Academic Press, New York, 65:499-560 (1980)].

The choice of a primer's nucleotide sequence depends on factors such as the distance on the nucleic acid from the region coding for the desired specific nucleic acid sequence present in a nucleic acid of interest and its hybridization site on the nucleic acid relative to any second primer to be used. The primer is preferably provided in single-stranded form for maximum efficiency, but may alternatively be double-stranded. If double-stranded, the primer is first treated to separate its strands before being used to prepare extension products. Preferably, the primer is a polydeoxyribonucleotide.

Polynucleotide as used herein is a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, RNA/DNA segments, oligonucleotides (relatively short polynucleotides), genes, vectors, plasmids, and the like.

Polynucleotides can be prepared by a variety of methods including de novo chemical synthesis and derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a polynucleotide can be conducted using any suitable method, such as, for example, the phosphotriester or phosphodiester methods. See Narang et al. [Meth. Enzymol. (1979) 68:90; U.S. Pat. No. 4,356, 270; Itakura et al., (1989) Ann. Rev. Biochem. 53:323-56; and Brown et al., (1979) Meth. Enzymol. 68:109].

Preferably, each of the primers used in the method of the invention comprises from about 4 to about 200 nucleotides in length. More preferably, each of said primers comprises from about 5 to about 50 nucleotides in length. Most preferably, each of said primers comprises from about 8 to about 30 nucleotides.

The enzymes employed in the method of the invention may be, for example, DNA ligase, for ligation reaction, preferably T4 ligase. During ligation, the DNA ligase covalently links hydrogen bonded double-stranded DNA molecules. This enzyme requires a 5' terminal phosphate to act as an electron acceptor.

For PCR amplification reaction, heat-stable (thermophilic) DNA polymerases are particularly preferred as they are stable in a most preferred embodiment in which PCR is conducted in a single solution in which the temperature is cycled. Representative heat-stable polymerases are the DNA polymerases isolated from *Bacillus stearothermophilus* (Bio-Rad, Richmond, Calif.), *Thermus thermophilus* (FIN-ZYME, ATCC #27634), *Thermus species* (ATCC #31674), *Thermus aquaticus* strain TV 1151 B (ATCC #25105), *Sulfolobus acidocaldarius*, described by Bukhrashuili et al., [Biochem. Biophys. Acta, 1008:102-7 (1989)] and by Elie et al., [Biochem. Biophys. Acta, 951:261-7 (1988)], *Thermus filiformis* (ATCC #43280), the polymerase isolated from *Thermus flavus* (Molecular Biology Resources; Milwaukee, Wis.), and "Vent" polymerases (New England Biolabs, Beverly, Me.). Taq DNA polymerase is available from a variety of sources including Perkin Elmer Cetus, (Norwalk, Conn.), Promega (Madison, Wis.) and Stratagene (La Jolla, Calif.), and AmpliTaq™ DNA polymerase is a recombinant Taq DNA polymerase available from Perkin-Elmer Cetus.

Particularly preferred is a high fidelity DNA polymerase having proof reading ability which is capable of polymerizing fragments of about 40 kd having minimal number of mutations. Such polymerases are commercially available, and include for example PFU (by Promega) and TaKaRa Ex Taq (TaKaRa). It may be preferred to use for the PCR reaction a polymerase that creates blunt-ends products. Polymerases leaving 3'-overhang products may be also employed in the present invention, however use of such T4 DNA polymerase will require exonuclease procedure to remove the 3'-overhang and create a blunt ended product.

According to a specific embodiment, the method of the invention is intended for constructing a construct comprising at least two segments of interest. Such segments may be for example, a segment of interest comprising an origin of replication (ori) sequence and optionally a sequence coding for a selectable marker, a segment comprising a sequence of interest and optionally a selectable marker; at least one additional segment comprising a nucleic acid heterologous or homologous coding sequence, or mutations, fragments or derivatives thereof; and optionally, at least one additional segment comprising nucleic acid sequences coding for expression, control, promoting and/or regulatory elements.

Thus, according to the invention, a DNA construct can include a bacterial origin of replication and bacterial antibiotic resistance markers, which allow for large-scale plasmid propagation in bacteria. A DNA construct which includes DNA encoding a selectable marker, along with additional control sequences, such as a promoter, polyadenylation site and splice junctions, can be used to confer a selectable phenotype.

Accordingly, the term control and regulatory elements includes promoters, terminators and other expression control elements. Such regulatory elements are described in Goeddel; [Goeddel et al., Gene Expression Technology: Methods in Enzymology 185, Academic Press, San Diego, Calif. (1990)]. For instance, any of a wide variety of expression control sequences that control the expression of a DNA sequence when operatively linked to it may be used in these vectors to express DNA sequences encoding any desired protein using the method of this invention Such regulatory sequences can be comprised of promoters, enhancers, scaffold-attachment regions, negative regulatory elements, transcriptional initiation sites, regulatory protein binding sites or combinations of said sequences. Furthermore, sequences which affect the structure of stability of the RNA or protein produced can be added. These sequences include polyadenylation signals, mRNA stability elements, splice sites, leader sequences for enhancing or modifying transport or secretion properties of the protein, or other sequences which alter or improve the function or stability of protein or RNA molecules.

As used herein, the term "homologous or heterologous coding sequence" or "gene" refers to a nucleic acid comprising an open reading frame encoding any desired gene constructed by the method of the present invention, including both exon and (optionally) intron sequences. The term "intron" refers to a DNA sequence present in a given gene, which is not translated into protein and, generally, is found between exons.

The heterologous or homologous coding sequence of interest according to the invention may encodes a protein selected from the group consisting of reporter proteins, enzymes, hormones, growth factors, cytokines, structural proteins and industrially applicable proteins, or itself be a therapeutic product.

Moreover, heterologous or homologous coding sequences incorporated into a construct by the present method may be DNA which encodes a translation or transcription product whose expression in cells is desired, or a portion of a translation or transcription product, such as a protein product or RNA product useful in treating an existing condition or preventing it from occurring (e.g., hGH or EPO); or DNA which does not encode a gene product but is itself useful, such as a transcriptional regulatory sequence or DNA useful to treat an existing condition or prevent it from occurring.

DNA sequences introduced to a construct according to the method of the invention can encode an entire desired product, or can encode, for example, active or functional portion(s) of the product. The product can be, for example, a hormone, a cytokine, an antigen, an antibody, an enzyme, a clotting factor, a transport protein, a receptor, a regulatory protein, a structural protein, a transcription factor, an antisense RNA, or a ribozyme. Additionally, the product can be a protein or a nucleic acid which does not occur in nature (i.e., a novel protein or novel nucleic acid). The DNA can be obtained from a source in which it occurs in nature or can be produced, by the genetic engineering techniques according to the invention. The DNA can encode one or more therapeutic products.

According to another specific embodiment, the heterologous coding sequence may encodes a reporter protein selected from the group consisting of green fluorescent protein (GFP), luciferase, secreted alkaline phosphatase (SEAP) and β-galactosidase (β-gal).

It is to be appreciated that the method of the invention may be used to construct segments comprising heterologous or homologous coding sequences, mutations derivatives and fragments thereof. Therefore, the method of the present invention may be used for constructing constructs having specific mutations, as described herein after.

By "derivatives" is meant the "fragments", "variants", "analogs" or "derivatives" of coding and/or non-coding region of said nucleic acid sequence. A "fragment" of a molecule, such as any of the DNA or cDNA sequences used by the method of the present invention, is meant to refer to any nucleotide subset of the molecule. A "variant" of such molecule is meant to refer to a naturally occurring molecule substantially similar to either the entire molecule or a fragment thereof. An "analog" of a molecule can be a homologous molecule from the same species or from different species. The amino acid sequence of an analog or derivative may differ from the original sequence, when at least one residue is deleted, inserted or substituted. Specifically, an analogue or derivative of the nucleic acid sequence that may be used by the method of the invention may comprise at least one mutation, point mutation, nonsense mutation, missense mutation, deletion, insertion or rearrangement. The coding region may be also altered by taking advantage of the degeneracy of the genetic code to alter the coding sequence such that, while the nucleotide sequence is substantially altered, it nevertheless encodes a protein having an amino acid sequence substantially similar to the disclosed fusion sequences.

It is to be appreciated that the total length of the DNA construct will vary according to the number of components (exogenous DNA, targeting sequences, selectable marker gene) and the length of each. The entire construct length will generally be at least 20 nucleotides.

The construct described herein, which contains a heterologous or homologous coding sequence, may be according to a specific embodiment of the invention, an expression vehicle.

"Expression Vehicles", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. As disclosed above, such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

Plasmids are the most commonly used form of vector but other forms of vectors which serves an equivalent function and which are, or become, known in the art are suitable for use herein. See, e.g., Pouwels et al., Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass (1988), which are incorporated herein by reference.

In general, such vectors contain in addition specific genes, which are capable of providing phenotypic selection in transformed cells. The use of prokaryotic and eukaryotic viral expression vectors is also contemplated.

The vector is introduced into a host cell by methods known to those of skilled in the art. Introduction of the vector into the host cell can be accomplished by any method that introduces the construct into the cell, including, for example, calcium phosphate precipitation, microinjection, electroporation or transformation. See, e.g., Current Protocols in Molecular Biology, Ausuble, F. M., ed., John Wiley & Sons, N.Y. (1989).

The method of the invention may be further employed for orientation-directed constructing of a mutated DNA construct, having at least one specific mutation. The specific mutation can be introduced to the construct during one of the PCR amplification reactions creating the initial blunt ended segments of interest. For point mutations, the desired mutation may be introduced through the primers used for the PCR reaction creating the segment of interest. Creation of a deletion mutation may be achieved using primers derived from regions, which do not include the region that should be deleted.

According to a preferred embodiment, the method of the invention may be performed manually.

In a specifically preferred embodiment, the method of the invention may be performed automatically.

A number of methods of the art of molecular biology are not detailed herein, as they are well known to the person of skill in the art. Such methods include site-directed mutagenesis, expression of cDNAs, analysis of recombinant proteins or peptides, transformation of bacterial cells, transfection of mammalian cells, and the like. Textbooks describing such methods are e.g., Sambrook et al., Molecular Cloning A Laboratory Manual, Cold Spring Harbor Laboratory; ISBN: 0879693096,1989, Current Protocols in Molecular Biology, by F. M. Ausubel, ISBN: 047150338X, John Wiley & Sons, Inc. 1988, and Short Protocols in Molecular Biology, by F. M. Ausubel et al. (eds.) $3^{rd}$ ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al. (eds), John Wiley & Sons. Inc., New York, N.Y.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures
Media
Luria-Bertani (LB) medium contained tryptone, yeast extract and NaCl at 10 g, 5 g and 10 g per liter, respectively. LB plates were supplemented with 20 mg per liter ampicillin for α-lactamase resistance.
Bacterial Strains
*E. coli* strain JM109 (Promega)
Enzymes
T4 DNA ligase (TaKaRa), T4 Polynucleotide Kinase (TaKaRa), Pfu DNA Polymerase (Promega), Restriction enzymes—PvuII and EcoRI (BioLab).

```
Primers

Primer 2037:  5'-GACTCTAGAGGATCCCCGG-3';       (SEQ ID
                                                NO:1)

Primer 2038:  5'-GACCTGCAGGCATGCAAGC-3';       (SEQ ID
                                                NO:2)

Primer 546:   5'-AATGGCTGGTGATCTTTCAGC-3';     (SEQ ID
                                                NO:3)

Primer 547:   5'-TCTAACATGTGTGTCGTTC-3';       (SEQ ID
                                                NO:4)

Primer 548:   5'-TTCTGTGATAAAGGGACC-3';        (SEQ ID
                                                NO:5)

Primer 549:   5'-GCACTTAGTCTTTGACC-3';         (SEQ ID
                                                NO:6)

Primer 335:   5'-GAACCCCGAGTGACAAGC-3';        (SEQ ID
                                                NO:7)

Primer 336:   5'-TCATACCAGGGCTTGGCC-3';        (SEQ ID
                                                NO:8)

Primer 826:   5'-GCTTCGTGCTTTGGACTACC-3';      (SEQ ID
                                                NO:9)

Primer 827:   5'-GGGCCCCAGGCAGCAGAACC-3';      (SEQ ID
                                                NO:10)

Primer 732:   5'-GCTGTTTCCTGTGTGAA-3',;        (SEQ ID
                                                NO:11)

Primer 110:   5'-AGCTGATACCGCTCGCCG-3';        (SEQ ID
                                                NO:12)

-continued
Primer 592:   5'-AATGAGTAAAGGAGAAGAAC-3';      (SEQ ID
                                                NO:13)

Primer 622:   5'-TATGACCATGATTACGCCA-3'.       (SEQ ID
                                                NO:14)
```

Preparation of Phosphorylated Primers
20 µg of primers were phosphorylated with 50 units of T4 Polynucleotide Kinase in the presence of 1 mM of ATP for 30 minutes at 37° C. The phosphorylation reaction was stopped by inactivation of the Kinase by incubation of the reaction for 20 minutes at 65° C. Primers were extracted with Tris-buffered phenol and precipitated with 0.1 volumes of 3 M KAc (pH 5.4) and 2.5 volumes of ice-cold ethanol. Phosphorylated primers were resuspended to 0.2 ng/µl in TE (10 mM Tris, pH 7.5, 1 mM EDTA).
PCR Reaction
PCR reaction was performed using 1 µM of each primer per 20 µl, 200 µM dNTP, 10 ng template DNA and 1.5 units of Pfu DNA polymerase in 1×Pfu polymerase buffer. PCR cycle conditions were 30 seconds at 92° C., 1 minute at 50° C., 3.5 minute at 72° C. for 25 cycles, followed by 10 minutes at 72° C.
Isolation of the PCR Product—Electroelution
Following PCR amplification, the PCR products were separated in agarose gel and the specific segment of interest was extracted using standard electroelution methods.
Ligation
Ligation reaction was performed in 20 µl of 1×T4 DNA ligase buffer containing 10 ng of each PCR product, 500 nM ATP and 400 Units T4 DNA ligase. The reaction was incubated for 30 minutes at 22° C. followed by heating for 10 minutes at 65° C.
Transformation and Plasmid Minipreparation
*E. coli* strain JM109 (100 µl) (Promega) was transformed with 10 µl of the self-ligation reaction and plated onto LB+Amp. The plates were incubated at 37° C. overnight. Ampicillin resistant colonies were passaged into 5 ml of LB+ampicillin and incubated overnight. Following incubation, the plasmids were isolated by standard mini-preparation protocols. After the plasmid mini-preparation the DNA was analyze with appropriate restriction enzyme. Following analyzes, the plasmid was purified by standard Large-scale plasmid DNA protocols.
Plasmid purification-Large-scale plasmid DNA and Miniprep plasmid DNA were purified by the alkaline lysis method [Birnboim, H. C., et al., Nucleic Acids Research, 7:1513-1522 (1979), Birnboim, H. C., Methods Enzymol. 100:243-255 (1983)].

Example 1

Creation of Constructs Having the Four Different Possible Orientations using the OER Method To create the first segment, a PCR reaction was performed using a human T-Cell cDNA library as a template, phosphorylated primers 335 (SEQ ID NO:7) and 336 (SEQ ID NO:8) and the high fidelity thermal stable polymerase Pfu DNA polymerase, that generated blunt ended product. Both primers were phosphorylated as described in the methods above.

The second segment was created by performing a PCR reaction using a Human T-Cell cDNA library as a template, phosphorylated primers 826 (SEQ ID NO:9) and 827 (SEQ ID NO:10). Following the PCR amplifications of both segments, PCR products were separated in 1.5% Agarose gel and the desired products (PCR product 1 of the first PCR reaction, PCR product 2 of the second PCR reaction) were extracted using standard electroelution methods (FIG. 2A).

A combined product comprising both segments was created by performing ligation reaction with the isolated PCR products described above. The ligation reaction product was amplified separately by four PCR reaction using the phosphorylated flanking primers 335 and 826 (SEQ ID:7 and SEQ ID:9, respectively), primers 335 and 827 (SEQ ID:7 and SEQ ID:10, respectively), primers 336 and 826 (SEQ ID:8 and SEQ ID:9, respectively) and primers 336 and 827 (SEQ ID:8 and SEQ ID:10, respectively) to generate a third DNA segment (FIG. 2B). Following the PCR amplification, the PCR products were separated in agarose gel and the specific segment was extracted by electro-elution. The combined product having the desired orientation was next analyzed using PvuII restriction enzyme. As shown in FIG. 2C, the resulting products had all the four possible orientations.

Example 2

Use of the OER Method in the Preparation of the Plasmids pcDNAPKRwt and the Mutated Plasmid pcDNAPKRΔ6

As an example for creation of constructs using the OER method of the invention, the pcDNAPKRwt as well as its corresponding mutated construct were constructed.

To create the first segment, a PCR reaction was performed using Plasmid pBlueScript (pBS) (Stratagene) as a template, phosphorylated primers 2037 (SEQ ID NO:1) and 2038 (SEQ ID NO:2) and the high fidelity thermal stable polymerase Pfu DNA polymerase, that generated blunt ended product. Both primers were phosphorylated as described in the methods herein above. This first DNA product comprises β-lactamase resistance gene (Amp$^r$) and the origin of replication region (Ori) from plasmid pBS was amplified by PCR.

The second segment was created by annealing of a Human T-Cell cDNA library with phosphorylated primers 546 (SEQ ID NO:3) and 547 (SEQ ID NO:4) in a cDNA concentration of 100 ng/μl, and performing a PCR reaction.

Following the PCR amplifications of both segments, PCR products were separated in 1% agarose gel and the desired products (PCR product 1 (Amp-Ori) from the first PCR reaction, PCR product 2 (PKRwt) from the second PCR reaction) were extracted using standard electroelution methods (FIG. 3A).

A combined product comprising both segments was created by performing ligation reaction with the isolated PCR products described above. The ligation reaction product was amplified by PCR using the phosphorylated flanking primers 2037 and 547 (SEQ ID:1 and SEQ ID:4, respectively), generating a third DNA segment (FIG. 3B). Following the PCR amplification, the PCR products were separated in agarose gel and the specific segment (PCR product: Amp-Ori-PKRwt) was extracted by electro-elution. The combined product having the desired orientation was next self ligated to create a double-strand DNA construct. Transformation to E. coli strain (Promega) was performed using the resultant plasmid, followed by mini-preparation of the DNA. Positive colonies were picked and further analyzed using EcoRI restriction enzyme. As shown in FIG. 3C, most of the colonies contained the plasmid pcDNAPKRwt having the desired orientation.

Preparation of Plasmid Containing Mutated cDNA of PKR (PKRΔ6):

As an example for insertion of mutation and creation of a mutated constructs using the OER method of the invention, the PKRΔ6 plasmid was next constructed.

The DNA plasmid pcDNAPKRwt (that was described above) was used as a template for PCR amplification. A blunt-ended product having the desired mutation (deletion mutation, in this case), was created using the phosphorylated flanking oligonucleotide primers 548 and 549 (denoted by SEQ ID NO:5 and 6, respectively). Following the PCR amplification, the PCR products were separated in agarose gel and the specific segment (PKR-Amp-Ori-PKR) was extracted using standard electroelution methods (FIG. 4A).

The combined product having the desired orientation was next self-ligated to create a double-stranded DNA construct. Transformation to E. coli strain (Promega) was performed using the resultant plasmid, followed by mini-preparation of the DNA. Positive colonies were picked and further analysed using EcoRI restriction enzyme. As shown in FIG. 4B, most of the colonies contained the plasmid pcDNAPKR□6 having the desired orientation.

Example 3

Use of Two Different Sets of Primers in Directing Desired Orientation of Two Different Constructs from the Same Template by the OER Method In order to exemplify the powerful use of the OER method in construction of two different plasmids having desired orientation from the same template, both pGFP-LacP-LacZ and the pLacZ-LacP-GFP plasmids were constructed, containing the β-galactosidase gene (LacZ), the IPTG induced promoter (LacP) and the green fluorescent protein (GFP).

Insertion of the LacP promoter by using orientation I (FIG. 5A), leads to expression of the β-galactosidase gene (LacZ), which results in blue color of the transformed colonies (FIG. 5D). Insertion of the LacP promoter by using orientation II (FIG. 5A), leads to GFP (green fluorescent protein) gene expression, which results in transformed colonies performing green fluorescent signal under UV light.

The LacP (IPTG induced promoter) segment was created by performing a PCR reaction using Plasmid pBlueScript (pBS) (Stratagene) as a template, phosphorylated primers 110 (SEQ ID NO:12) and 732 (SEQ ID NO:11) as well as the high fidelity thermal stable polymerase Pfu DNA polymerase, that generates a blunt-ended product. Both primers are phosphorylated as described in the methods above.

The second segment was created by second PCR reaction using Plasmid pLacZ-GFP (pLG) (Gene Bio-Application) as a template, phosphorylated primers 622 (SEQ ID NO:14) and 592 (SEQ ID NO:13) and the high fidelity thermal stable polymerase Pfu DNA polymerase. This DNA fragment comprises the Lac Z, the β-lactamase resistance gene (Ampr), the origin of replication region (Ori) and GFPuv genes (FIG. 5A).

Following the PCR amplifications of both segments, PCR products were separated in 1% agarose gel and the desired products (PCR product 1 (LacP) from the first PCR reaction and PCR product 2 (LacZ-Amp$^r$-Ori-GFP) from the second PCR reaction were extracted using standard electro-elution methods.

A combined product comprising both segments was created by performing ligation reaction with the isolated PCR products described above. The ligation reaction product was amplified by two separate PCR reactions using the phosphorylated flanking primers 592 and 110 (SEQ ID NO:13 and SEQ ID NO:12, respectively) generating a third DNA segment (LacP to LacZ) as shown by FIG. 5B or 592 and 732 (SEQ ID NO:13 and SEQ ID NO:11, respectively) generating a third DNA segment (LacP to GFPuv) as shown by FIG. 5C. Following the PCR amplification, the PCR products were separated in agarose gel and the specific segments (PCR product 1: GFP-Amp-Ori-LacP-LacZ, PCR product 2: LacZ-Amp-Ori-LacP-GFP) were extracted by electro-elution. The combined products having the desired orientation were next self ligated to create a double-strand DNA constructs. Transformation of *E. coli* strain (Promega) with the two different constructs was next performed. As shown in FIG. 5D, most of the pGFP-LacP-LacZ plasmid transformed colonies performed a blue color and most of the pLacZ-LacP-GFP plasmid transformed colonies displayed a green color under UV light. Thus, the OER method of the present invention performed versatility and high efficiency in creation of constructs having a desired orientation from identical template.

What is claimed is:

1. A method for orientation-directed construction of a construct comprising at least two nucleic acid segments of interest, which method comprises the steps of:
   a. providing products having phosphorylated blunt ends derived from said nucleic acid segments of interest;
   b. performing separate ligation reactions, wherein in each reaction the phosphorylated blunt-ended products of two different segments obtained in step (a) are ligated to create a combined ligated sequence;
   c. performing PCR amplification reaction using said combined ligated sequence obtained in step (b) as a template and specific enrichment primers directing said PCR amplification towards the desired orientation of the complete combined ligated sequences, wherein each combined ligated sequence is amplified in a separate reaction creating a combined product having phosphorylated blunt ends;
   d. isolating and purifying said combined product having the enriched desired orientation obtained in step (c); and
   e. performing self-ligation of said isolated purified combined product obtained in step (d), creating a circular double-stranded DNA construct containing the desired segments properly aligned and operably linked.

2. A method according to claim 1, wherein a first said segment of interest comprises a replicable segment, and said first segment of interest and/or any other said segment of interest comprises a sequence coding for a selectable marker.

3. A method according to claim 1, wherein said phosphorylated blunt-ended products of step (a) are obtained by any one of:
   (i) performing a first set of PCR amplification using said segments as template, to create products having phosphorylated blunt ends, wherein each segment is amplified in a separate reaction, using specific primers;
   (ii) creating blunt-ended products by cleaving said nucleic acid segments employing a blunt-end endonuclease;
   (iii) creating cohesive end products by cleaving said nucleic acid segments employing a sticky-end endonuclease, followed by fill-in reaction; and
   (iv) creating cohesive end products by cleavage of said nucleic acid segments employing a sticky-end endonuclease, followed by single-strand DNA endonuclease reaction and degrading single-strand extensions from the DNA ends.

4. A method according to claim 3, wherein said phosphorylated blunt-ended products are obtained by phosphorylation of any one of the blunt-ended PCR products in step (i) or the PCR primers by employing T4 kinase.

5. The method according to claim 1, wherein said construct comprises more than two nucleic acid segments, which method comprises the steps of:
   a. cyclic repititiom of steps (a) to (d) as defined in claim 1, to create the isolated combined products having the desired orientation;
   b. performing separate ligation reactions, wherein in each ligation reaction the PCR products of two of the combined products obtained in step (a) are ligated to create a combined ligated sequence;
   c. performing PCR reaction using said combined ligated sequence obtained in step (b) as a template, and specific enrichment primers directing said PCR amplification towards the desired orientation of the complete combined ligated sequences, wherein each combined ligated sequence is amplified in a separate reaction creating a combined product;
   d. isolating and purifying said combined products having the desired orientation obtained in step (c); and
   e. performing self-ligation of said isolated final combined product obtained in step (e), creating a circular double-stranded DNA construct containing the desired segments properly aligned and operably linked.

6. The method according to claim 2, wherein said replicable segment comprises an origin of replication (ori) sequence.

7. The method according to claim 6, wherein said replicable segment is derived from a replicable vector selected from the group consisting of retroviral vectors, phage vectors, plasmid vectors, expression vectors, self replicating vectors, phagemid vectors and YAC vectors.

8. The method according to claim 1, wherein said specific primers employed in the first set of PCR amplification reactions (steps (a) to (d)) are: a 5' primer comprising a sequence derived from the 5' end of a segment of interest (sense primer) and a 3' primer which is complementary to the sequence of the 3' end of the specific segment to be amplified (antisense primers).

9. The method according to claim 1, wherein said specific enrichment primers employed in the amplification of the combined ligated sequences are:
  (i) a 5' primer comprising a sequence derived from 5' end of the first segment, which is upstream to the second ligated segment in the combined ligated product (sense primer); and
  (ii) a 3' primer which is complementary to the 3' end sequence of the second ligated segment (anti-sense primer), of the combined ligated sequence.

10. The method according to claim 8, wherein each of said primers comprises from about 4 to about 200 nucleotides in length.

11. The method according to claim 9, wherein each of said primers comprises from about 4 to about 200 nucleotides in length.

12. The method according to claim 10, wherein each of said primers comprises from about 8 to about 30 noeleorides in length.

13. The method according to claim 1, wherein said ligation reaction is performed by employing DNA ligase.

14. The method according to claim 1, wherein said PCR amplification is performed by employing a high fidelity DNA polymerase.

15. The method according to claim 1, wherein said construct comprises:
  a. one of said segments of interest comprising an origin of replication (ori) sequence and a sequence coding for a selectable marker;
  b. at least one additional segment comprising a heterologous or homologous coding nucleic acid sequence of interest, or mutations, fragments or derivatives thereof and c. optionally, at least one additional segment comprising nucleic acid sequences coding for expression, control, promoting and/or regulatory elements.

16. The method according to claim 15, wherein said heterologous or homologous coding sequence of interest encodes a protein selected from the group consisting of reporter proteins, enzymes, hormones, growth factors, cytokines, and structural proteins, or is itself a therapeutic product.

17. The method according to claim 16, wherein said heterologous coding sequence encodes a reporter protein selected from the group consisting of green fluorescent protein (GFP), luciferase, secreted alkaline phosphatase (SEAP) and β-galactosidase (β-gal).

18. The method according to claim 14, wherein said construct is an expression vehicle.

19. The method of claim 1, wherein said method is performed manually.

20. The method of claim 1, wherein said method is performed automatically.

21. The method of claim 1, wherein steps (b) to (d) are cyclically repeated a plurality of times to create a combined product containing all the nucleic acid segments aligned in the desired orientation to create a final combined product.

22. The method of claim 1, further comprising the step of cyclic repetition of steps (b) to (d) for a desired number of times, to create the isolated combined product having the desired orientation, before performing a self-ligation (step e).

* * * * *